US009842390B2

(12) United States Patent
Syeda-Mahmood

(10) Patent No.: US 9,842,390 B2
(45) Date of Patent: Dec. 12, 2017

(54) AUTOMATIC GROUND TRUTH GENERATION FOR MEDICAL IMAGE COLLECTIONS

(71) Applicant: International Business Machines Corporation, Armonk, NY (US)

(72) Inventor: Tanveer F. Syeda-Mahmood, Cupertino, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 109 days.

(21) Appl. No.: 14/615,512

(22) Filed: Feb. 6, 2015

(65) Prior Publication Data

US 2016/0232658 A1 Aug. 11, 2016

(51) Int. Cl.
*G06K 9/62* (2006.01)
*G06T 7/00* (2017.01)
(Continued)

(52) U.S. Cl.
CPC ...... *G06T 7/0012* (2013.01); *G06F 17/30247* (2013.01); *G06F 19/321* (2013.01);
(Continued)

(58) Field of Classification Search
USPC ....... 382/103, 115, 128, 131, 132, 155, 158, 382/159, 173, 181; 706/12, 20, 45, 112;
(Continued)

(56) References Cited

U.S. PATENT DOCUMENTS 6,111,983 A 8/2000 Fenster et al.
7,167,823 B2 * 1/2007 Endo ................ G06F 17/30265 704/7

(Continued)

FOREIGN PATENT DOCUMENTS

WO 2006054267 A1 5/2006
WO 2013037983 A1 3/2013

OTHER PUBLICATIONS

Alomari et al., "Toward a clinical lumbar CAD: herniation diagnosis", Received Jan. 12, 2010 / Accepted: May 4, 2010 / published onlin Jun. 11, 2010; Int J CARS (2011) 6: pp. 119-126.

(Continued)

*Primary Examiner* — Xuemei Chen
(74) *Attorney, Agent, or Firm* — Cantor Colburn LLP

(57) ABSTRACT

Methods and arrangements for automatic ground truth generation of medical image collections. Aspects include receiving a plurality of imaging studies, wherein each imaging study includes one or more images and a textual report associated with the one or more images. Aspects also include selecting a key image from each of the one or more images from each of the plurality of imaging studies and extracting one or more discriminating image features from a region of interest within the key image. Aspects further include processing the textual report associated with the one or more images to detect one or more concept labels, assigning an initial label from the one or more concept labels to the one or more discriminating image features, and learning an association between each of the one or more discriminating image features and the one or more concept labels.

18 Claims, 6 Drawing Sheets

(51) Int. Cl.

| | |
|---|---|
| ***G06K 9/46*** | (2006.01) |
| ***G06K 9/00*** | (2006.01) |
| ***G06F 17/30*** | (2006.01) |
| ***G06F 19/00*** | (2011.01) |

(52) U.S. Cl.
CPC ........... *G06K 9/00751* (2013.01); *G06K 9/46* (2013.01); *G06K 9/4676* (2013.01); *G06K 9/627* (2013.01); *G06K 9/6255* (2013.01); *G06K 9/6267* (2013.01); *G06K 2009/4666* (2013.01); *G06T 2207/20081* (2013.01)

(58) Field of Classification Search
USPC .................................................. 707/722, 739
See application file for complete search history.

(56) References Cited

U.S. PATENT DOCUMENTS

| | | | | |
|---|---|---|---|---|
| 7,412,429 | B1 * | 8/2008 | Syeda-Mahmood | G06K 9/6226 706/45 |
| 7,428,541 | B2 * | 9/2008 | Houle | G06F 17/30011 |
| 7,912,288 | B2 * | 3/2011 | Winn | G06K 9/342 382/173 |
| 8,379,994 | B2 * | 2/2013 | Dai | G06K 9/6262 382/158 |
| 8,687,851 | B2 * | 4/2014 | Hua | G06K 9/00677 382/103 |
| 8,712,122 | B2 * | 4/2014 | Syeda-Mahmood | G06T 7/0016 382/128 |
| 8,744,152 | B2 * | 6/2014 | Beymer | G06T 3/4053 375/240.08 |
| 8,793,199 | B2 * | 7/2014 | Syeda-Mahmood | G06F 19/3443 706/12 |
| 8,798,375 | B1 * | 8/2014 | Chang | G06K 9/6202 382/181 |
| 8,831,352 | B2 * | 9/2014 | Gao | G06K 9/00671 382/115 |
| 8,849,790 | B2 * | 9/2014 | Bellare | G06F 17/3028 706/45 |
| 8,886,576 | B1 * | 11/2014 | Sanketi | G06F 17/30038 706/12 |
| 9,082,047 | B2 * | 7/2015 | Marchesotti | G06K 9/627 |
| 9,171,018 | B2 * | 10/2015 | Ovsjanikov | G06F 17/30277 |
| 9,218,546 | B2 * | 12/2015 | Zhang | G06K 9/74 |
| 9,230,194 | B2 * | 1/2016 | Rabinovich | G06K 9/66 |
| 9,232,205 | B2 * | 1/2016 | Suzuki | G06K 9/00718 |
| 9,250,993 | B2 * | 2/2016 | Mani | G06F 11/0793 |
| 9,280,709 | B2 * | 3/2016 | Suzuki | G06K 9/00718 |
| 9,342,592 | B2 * | 5/2016 | Giverts | G06F 17/3071 |
| 9,349,105 | B2 * | 5/2016 | Beymer | G06N 99/005 |
| 2009/0148007 | A1 | 6/2009 | Zhao et al. | |
| 2009/0148010 | A1 | 6/2009 | Boroczky et al. | |
| 2011/0182493 | A1 * | 7/2011 | Huber | G06F 19/3487 382/132 |
| 2012/0027288 | A1 | 2/2012 | Yuan et al. | |
| 2012/0039527 | A1 * | 2/2012 | Qi | G06K 9/4676 382/159 |
| 2013/0132315 | A1 * | 5/2013 | Principe | G06N 7/00 706/20 |
| 2015/0169641 | A1 * | 6/2015 | Alldrin | G06F 17/30268 707/750 |
| 2015/0220543 | A1 * | 8/2015 | Chechik | G06F 17/30781 707/722 |
| 2015/0331929 | A1 * | 11/2015 | El-Saban | G06F 17/30598 707/739 |
| 2015/0363671 | A1 * | 12/2015 | Ma | G06N 99/005 382/155 |
| 2016/0063538 | A1 * | 3/2016 | Srivastava | G06Q 30/0244 705/14.43 |
| 2016/0063720 | A1 * | 3/2016 | Han | G06T 7/0079 382/131 |
| 2016/0125273 | A1 * | 5/2016 | Matsunaga | G06K 9/6269 382/159 |
| 2016/0217344 | A1 * | 7/2016 | Misra | G06K 9/6227 |
| 2016/0292148 | A1 * | 10/2016 | Aley | G06F 17/276 |

OTHER PUBLICATIONS

Cui et al., "Fluoroscopic gating without implanted fiducial markers for lung cancer radiotherapy based on support vector machines", IOP Publishing; Phys. Med. Biol. 53 (2008) pp. N315-N327.

Disclosed Anonymously, "Imaging Phantom for Management of Non-Rigid Motion Errors", an IP.com Prior Art Database Technical Disclosure; IP.com No. IPCOM000222907D; IP.com Electronic Publication: Oct. 29, 2012; pp. 1-11.

Foncubierta-Rodriguez et al., "Ground Truth Generation in Medical Imaging a Crowdsourcing-based Iterative Approach", CrowdMM' 12, Oct. 29, 2012; Nara, Japan, 6 pages.

Giancardo, et al., "Exudate-based diabetic macular edma detection in fundus images using publicly available datasets", Medical Image Analysis 16 (2012) pp. 216-226.

Siemens AG; Juergen Carstens A Method for Composition of Medical Imaging Volumes Using Selective Blending; An IP.com Prior Art Database Technical Disclosure; Original Publication Date: Jul. 13, 2011; IP.com No. IPCOM000208568D; IP.com Electronic Pub.

Tobon-Gomez et al., "Automatic training and reliability estimation for 3D ASM applied to cardiac MRI segmentation", Published: Jun. 1, 2012; Physics in Medicine and Biology 57 (2012); pp. 4155-4174.

Yang et al., "Method and Apparatus for Evaluating the Quality of Medical Imaging Systems and Components Using Model Observers and Computer Aided Detection Algorithms" An IP.com Prior Art Database Technical Disclosure; IP.com No. IPCOM000130693D; IP.c.

* cited by examiner

| Disease Label | Sentence detected to contain the disease label |
|---|---|
| Aortic sclerosis,Aortic stenosis | Marked aortic sclerosis present with evidence of stenosis. |
| Fracture of clavicle | There is a transverse fracture of the mid left clavicle with mild superior angulation of the fracture fragment. |
| Perforation of Esophagus | A contrast esophagram shows esophageal perforation of the anterior left esophagus at C4-5 with extraluminal contrast seen. |
| Edema of lower extremity | Extremities: Lower extremity trace pitting edema and bilateral lower extremity toe ulceration. |
| Atrial dilatation | Left atrium: Left atrial size is mildly dilated. |
| Abnormal findings in lung | abn findings-lung field. |

FIG. 4A

| | | | | | |
|---|---|---|---|---|---|
| tricuspid regurgitation | 2465 | secondary pulmonary hypertension | 167 | ventricular septal defect | 41 |
| mitral regurgitation | 2421 | tricuspid insufficiency | 127 | ventricular hypertrophy | 38 |
| aortic insufficiency | 1320 | marked aortic sclerosis | 115 | congestive heart failure | 37 |
| left ventricular hypertrophy | 1043 | pleural effusion | 93 | pulmonary stenosis | 36 |
| aortic sclerosis | 1023 | pulmonic insufficiency | 93 | right ventricular hypertrophy | 34 |
| aortic stenosis | 718 | bundle branch block | 93 | left pleural effusion | 32 |
| pulmonary hypertension | 525 | left bundle branch block | 87 | mitral prolapse | 32 |
| pericardial effusion | 338 | cardiomyopathy | 64 | dilated cardiomyopathy | 30 |
| mitral stenosis | 331 | myocardial infarction | 58 | atrial septal aneurysm | 30 |
| mitral insufficiency | 322 | ischemia | 53 | syncope | 28 |
| atrial fibrillation | 308 | patent foramen ovale | 43 | hypertrophy | 28 |
| aortic regurgitation | 287 | coarctation | 41 | atrial flutter | 26 |

FIG. 4B

Algorithm 1 Longest Common Subfix Algorithm

LCF(S,T):

1: Initialize $c[i, 0] = 0, c[0, j] = 0, 0 \leq i \leq K, 0 \leq j \leq N.$

2: Iterate for $(1 \leq i \leq K)$ for $(1 \leq j \leq N)$ $$\rho_{ij} = \frac{|Pmax\,(i,j)\,|}{max\{|s_{i}|,|t_{j}|]}$$

If $c[\, i - 1, j - 1] + \rho_{ij} > C[i - 1, j]$ and $C[i - 1, j - 1] + \rho_{ij} > C[i, j - 1]$ $C[i, j] = C[i - 1, j - 1] + \rho_{ij}$ else if $(C[i - 1, j] + \rho_{ij} > C[i, j - 1]$ $C[i, j] = C[i - 1, j] - \delta$ else $C[i, j] = C[i, j - 1] - \delta$

FIG. 5

AUTOMATIC GROUND TRUTH GENERATION FOR MEDICAL IMAGE COLLECTIONS

BACKGROUND

The present invention relates to processing of medical images, and more specifically, to automatic ground truth generation for medical image collections.

The medical imaging community has traditionally lagged behind the general computing community on the testing of methods on large collections of data. This was both due to the difficulty of acquiring the image collections and the availability of clinical experts for ground truth labeling. With electronic health records (EHR) being rolled out in many large hospitals, it is now possible to obtain large scale collections of DICOM imaging studies in integrated EHR systems. However, effectively assigning ground truth disease labels to such collections presents many challenges. It is tedious and impractical to expect clinical experts to manually label these images individually. In addition, manual data entry may also be error-prone when consensus is lacking among experts. Unlike general imaging, many medical images need deep clinical interpretation expertise which is difficult to achieve through conventional large-scale ground truthing mechanisms such as crowd-sourcing. Yet, obtaining these ground truth labels is important for a number of applications such as clinical decision support, computer-aided diagnosis and precision measurement extraction.

In most cases, electronic health record systems include textual reports such as clinical notes, radiology and cardiology reports documenting the findings in medical imaging studies are often available. In general, these reports document many diseases and findings in the echocardiogram images including both positive and negative findings.

BRIEF SUMMARY

Exemplary embodiments include methods, systems and computer program products for automatic ground truth generation of medical image collections. Aspects include receiving a plurality of imaging studies, wherein each imaging study includes one or more images and a textual report associated with the one or more images. Aspects also include selecting a key image from each of the one or more images from each of the plurality of imaging studies and extracting one or more discriminating image features from a region of interest within the key image. Aspects further include processing the textual report associated with the one or more images to detect one or more concept labels, assigning an initial label from the one or more concept labels to the one or more discriminating image features, and learning an association between each of the one or more discriminating image features and the one or more concept labels.

For a better understanding of exemplary embodiments of the invention, together with other and further features and advantages thereof, reference is made to the following description, taken in conjunction with the accompanying drawings, and the scope of the claimed embodiments of the invention will be pointed out in the appended claims.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 4A is a chart illustrating the results of applying a longest common subfix algorithm on a variety of sentences found in textual reports in accordance with an exemplary embodiment;

FIG. 4B is a chart illustrating a frequency distribution of top disease labels found in cardiac reports in accordance with an exemplary embodiment;

FIG. 5 depicts an algorithm for determining a longest common subfix in accordance with an exemplary embodiment.

DETAILED DESCRIPTION

Figure 1:
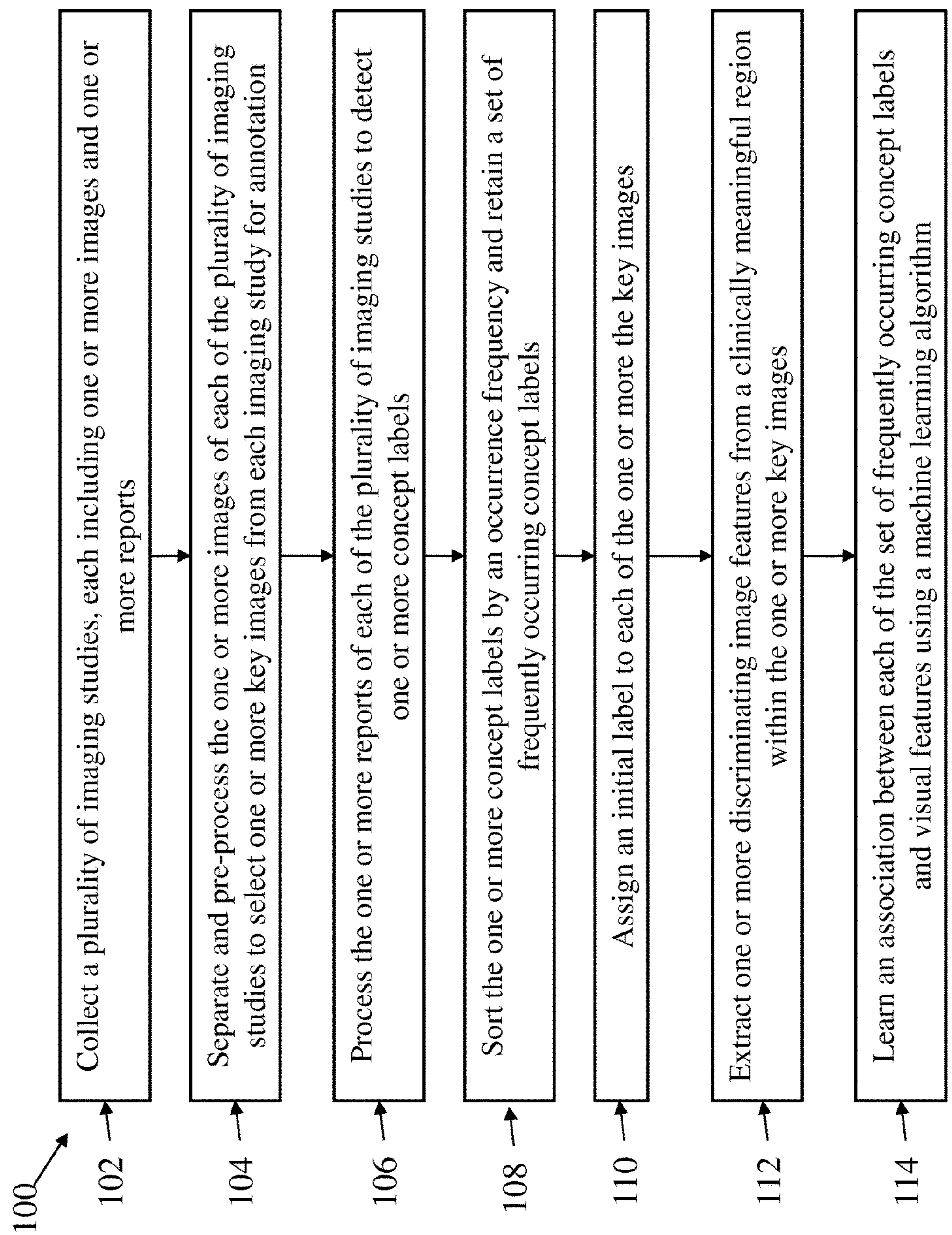
FIG. 1 depicts a flow chart of a method for automatic ground truth generation of medical image collections in accordance with an exemplary embodiment.

Exemplary embodiments include methods, systems and computer program products for automatic ground truth generation of medical image collections. The method includes automatically extracting disease labels from textual reports of an imaging study and assigning the extracted disease labels as ambiguous, or initial, labels to associated images within the imaging study. The method also includes extracting diagnostically relevant visual features from the associated images of the imaging study. In exemplary embodiments, the features are extracted by automatically extracting Doppler envelopes and encoding their enclosing regions through Scale-Invariant Feature Transform (SIFT) code books. The method also includes learning the association between common disease labels and visual features using a machine learning algorithm. In exemplary embodiment, the machine learning algorithm is a convex optimization learning algorithm that minimizes a surrogate loss appropriate for the ambiguous labels.

In exemplary embodiments, textual reports that include clinical interpretations are provided for an imaging study, such as an echocardiogram study. By automatically extracting the diagnoses of diseases in the textual reports, the reports can be used as a source for labeling the images of the study associated with the reports. However, such a label set will at best be an ambiguous label set since the correspondence between images of the diagnostic imaging study and the disease labels is unknown.

In one exemplary system, Doppler spectrum in cardiac ultrasound is used to measure blood flow velocity, direction, and turbulence within the heart chambers and through the valves. The velocity patterns are observed by clinicians to diagnose many conditions, including blood clots or thrombus, poorly functioning valves, heart valve defects, etc. Automatic detection of such visual patterns can further narrow the list of possible disease labels derived from reports. Since the label set derived from report is potentially applicable more than one image in the study, because the report is for the entire study and not specifically targeted to a single image, a systematically machine learning formulation of learning from partial labels can be used to reduce the overall ambiguity in association and correspondence. Such a learning algorithm can exploit the similarities in appearance of images with overlapping disease labels assuming similar diseases show similar image patterns, which has already been observed for cardiac Doppler patterns by other researchers. In exemplary embodiments, the automatic detection of vocabulary phrases will be tolerant to the word variations based on rules of grammar (English, in this case) for tenses, active or passive voices, singular or plural while still retaining the semantics. Furthermore, the matching of the text in the reports should be robust to a few missing words or presence of extra words as different clinicians may use slightly different words to describe a similar diagnosis.

Referring now to FIG. 1, a flowchart diagram of a method 100 for automatic ground truth generation of medical image collections in accordance with an exemplary embodiment is shown. As shown at block 102, the method 100 includes collecting a plurality of imaging studies, each imaging study including one or more images and one or more reports. Next, as shown at block 104, the method 100 includes separating and pre-processing the one or more images of each of the plurality of imaging studies to select one or more key images from each imaging study for annotation. In addition, as shown at block 106, the method includes processing the one or more reports of each of the plurality of imaging studies to detect one or more concept labels. The one or more concept labels are then sorted by an occurrence frequency and a set of frequently occurring concept labels is retained, as shown at block 108. Next, as shown at block 110, the method 100 includes assigning an initial label to each of the one or more the key images, wherein the initial label is selected from the one or more concept labels detected in the associated textual report. In exemplary embodiments, a set of images from the same study may be assigned the same labels initially. The method 100 further includes extracting one or more discriminating image features from a clinically meaningful region, or region of interest, within the one or more key images, as shown at block 112. Next, the method 100 includes, learning an association between each of the set of frequently occurring concept labels and visual features using a machine learning algorithm, as shown at block 114. In exemplary embodiments, the machine learning algorithm is a convex optimization learning formulation that minimizes a surrogate loss appropriate for the ambiguous labels.

Figure 2:
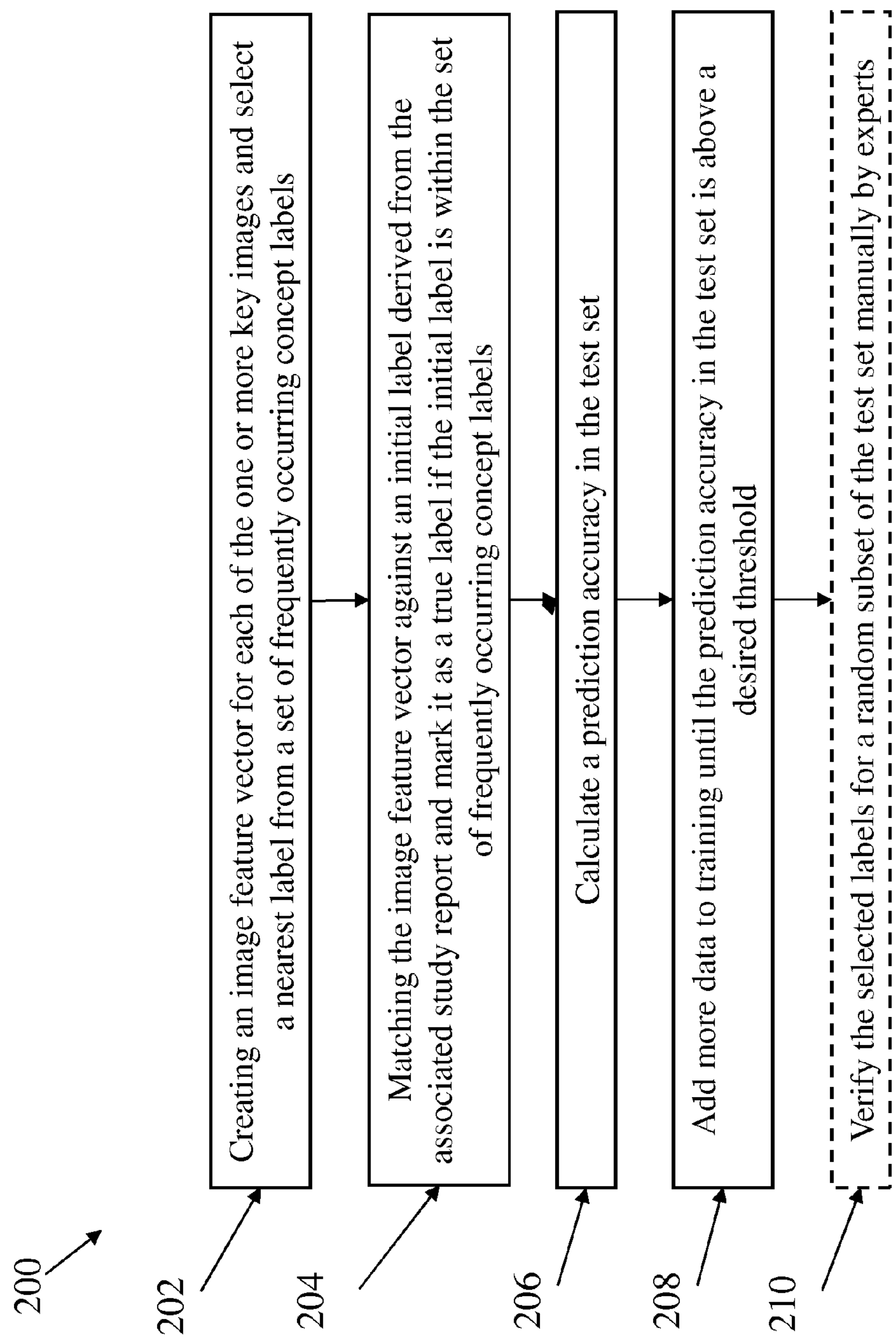
FIG. 2 depicts a flowchart diagram of method for learning an association between a set of frequently occurring concept labels and visual features of an imaging study in accordance with an exemplary embodiment.

Referring now to FIG. 2, a flowchart diagram of a method 200 for learning an association between a set of frequently occurring concept labels and visual features of an imaging study in accordance with an exemplary embodiment is shown. As shown at block 202, the method 200 includes creating an image feature vector for each of the one or more key images and selecting the nearest labels from a set of frequently occurring concept labels. Next, as shown at block 204, the method 200 includes matching the image feature vector against an initial label derived from the associated study report and marking it as a true label if the initial label is within the set of frequently occurring concept labels. Next, as shown at block 206, the method 200 includes calculating a prediction accuracy of the overall test set. In exemplary embodiments, the prediction accuracy of the overall test set can be determined by a percentage of the initial labels that are marked as true labels. As shown at block 208, the method 200 includes adding more data to the training set until the prediction accuracy in the overall test set is above a desired threshold. Next, as shown at block 210, the method 200 optionally includes verifying the selected labels for a random subset of the test set manually by experts.

In exemplary embodiments, disease label detection in textual reports uses a vocabulary of disease terms assembled from standards such as SNOMED CT and ICD9. To spot the occurrence of the disease phrase within natural language sentences in reports, a string matching algorithm referred to herein as the longest common subfix algorithm is used. Given a query vocabulary phrase S=<s1s2 . . . sK> of K words and a candidate sentence T=<t1t2 . . . tN> of N words, longest common subfix is defined as LCF (S, T)=<p1p2 . . . pL>, where L is the largest subset of words from S that found a partial match in T and pi is a partial match of a word si∈S to a word in T. A word si in S is said to partially match a word tj in T if it shares a maximum length common prefix pi such that:

$$\frac{|p_i|}{\max\{|s_i|, |t_j|\}} > \tau.$$

If the threshold τ=1.0, this reduces to the case of finding exact matches to words of S. Using dynamic programming to implements the longest common subfix algorithm, the best alignment between a vocabulary phrase S and candidate sentence T is found by keeping an array C[i, j] to calculate the score of matching a fragment of S up to the ith word and fragment of T up to the jth word. The dynamic programming matrix is then updated according to the algorithm shown in Algorithm 1, shown in FIG. 5. Here pmax(i, j) is the longest prefix of the strings (si, tj) and δ is a mismatch penalty, which controls the separation between matched words and prevents words that are too far apart in a sentence from being associated with the same vocabulary phrase. Using this algorithm, a vocabulary phrase S is said to be detected in a sentence T if $$\frac{|LCF(S, T)|}{|S|} \geq \Gamma$$

For some threshold Γ. The choice of τ and Γ affect precision and recall in matching and was chosen to meet specified criteria for precision and recall based on an ROC curve analysis on labeled collection.

FIG. 4A illustrates a table showing the results of applying the longest common subfix algorithm on a variety of sentences found in exemplary textual reports. It can be seen that the algorithm was able to spot the occurrence of both aortic sclerosis and aortic stenosis in the first sentence, even though the words aortic and stenosis are separated by several words in between. Similarly, the vocabulary phrase left atrial dilatation was matched to 'Left Atrium: Left atrial size is mildly dilated' even without deep understanding of the linguistic origins of the underlying words. In general the longest common subfix algorithm achieves high precision and recall by use of many refinements including patterns for spotting negations and common prefixes for fast word finding.

By analyzing the disease labels derived from a large collection of echocardiogram reports, those with 1% chance of occurrence were retained to form the reference list of the top thirty six candidate disease labels. The Doppler images from an echocardiogram study were then labeled with a subset of these as appropriate from the result of disease label detection in the corresponding reports. FIG. 4B depicts a table showing the top thirty-six disease labels detected in a collection of 7148 echocardiogram reports used an experiment. While the majority of diseases in this set are inferable from Doppler imaging, there are sufficient distractions (e.g. syncope, ischemia) to allow a good test bed for disambiguation using learning later.

For Doppler images of an echocardiogram study, the clinically relevant region is the Doppler spectrum. The shape of the velocity pattern, its amplitude (scale), as well as its density conveys important discriminatory information about diseases. The method used for extracting Doppler spectrum uses the same pre-processing steps of region of interest detection, EKG extraction, periodicity detection, and envelope extraction and also includes building a common Doppler reference frame and feature extraction from the Doppler spectrum. In exemplary embodiments, since the amplitude of Doppler velocity is important for disease discrimination, the amplitude units from the text calibration markers on Doppler images can be recovered using an optical character recognition algorithm.

In exemplary embodiments, building a common Doppler reference frame includes render the recovered velocity values in a common reference frame for feature extraction and comparison. In exemplary embodiments, the pixels in the Doppler spectrum region are transformed using a similarity to a reference image of fixed size (WM×HM) corresponding to the maximum range of velocities VM=VMa− VMb. Then given any single period Doppler spectrum image of size (WI×HI) representing a range of velocities=VI=(VIa−VIb) where the suffix a and b refer to direction, every pixel point (x, y) can be linearly transformed to a point (xi, yi) as yi=sh*y+thxi=sw*x+tw where sw=WM/WI, tw=0, since all the spectra are aligned with respect to the start of the R-wave. Also, sh=VI/Vm*Hm/HI and th=0.5*HM−y0, where y0 is the baseline for the Doppler spectrum.

In many Doppler images, the envelopes can be faint and broken due to imaging artifacts, or may be subject to aliasing. In exemplary embodiments, feature extraction from the Doppler spectrum includes densely sampling both an envelope and an interior of the Doppler spectrum using the SIFT features. The SIFT descriptor models the location, scale, orientation and intensity gradient information to capture clinically observed variations in intensity and shape in the interior (outflow tract) and boundaries of the Doppler spectrum. Due to the high dimensionality of SIFT features, the SIFT features were clustered to form code books similar to a bag of words model.

Given a set of feature vectors X={xi}, i=1 . . . N corresponding to all training images, where each sample xi is associated with a set of ambiguous labels Yi={aij}, j=1 . . . Mi, the problem is to train a classifier that could reduce the ambiguity and obtain at least one label for sample from X. Let the set of possible labels be {1, 2 . . . , L}. Using a convex optimization formulation, for each class label a, a linear classifier is defined as ga(x)=wa·x. Given scores from all the classifiers {ga(x)} for a sample x, one could obtain the best label as arg maxa ga(x). The overall classifier is denoted as g(x), which is parameterized by {ga(x)} or d×L parameters. Many formulations of fully-supervised multi-class learning have been proposed based on minimization of convex upper bounds on risk, usually, called the 0/1 loss to indicate the probability of making an error in class labeling.

When ambiguous labels are present, as long as the predicted label for xi belongs to Yi, it is considered a correct classification. The parameters of g are learned by minimizing the following objective function:

$$\min_w \frac{1}{2}\|w\|_2^2 + C\|\xi\|_2^2 \tag{1}$$

such that $$\text{s.t. } \frac{1}{|Y_i|}\sum_{a \in Y_i} w^a \cdot x_i \geq 1 - \xi_i - w^a \cdot x_i \geq 1 - \xi_{ia} \forall\, a \notin Y_i.$$

Here w is a concatenation of $\{w^a\}$. Once this classifier has been trained, given a new sample x, its classification score can be obtained with respect to each of the labels, since all $w^a$ are now known. Note that this approach is different from training a single SVM for each label or a multi-class SVM, since the best learner is chosen based on minimizing the empirical risk from the ambiguous 0/1 loss defined over the ambiguous label set as shown by the summation term in Equation 1.

Figure 3:
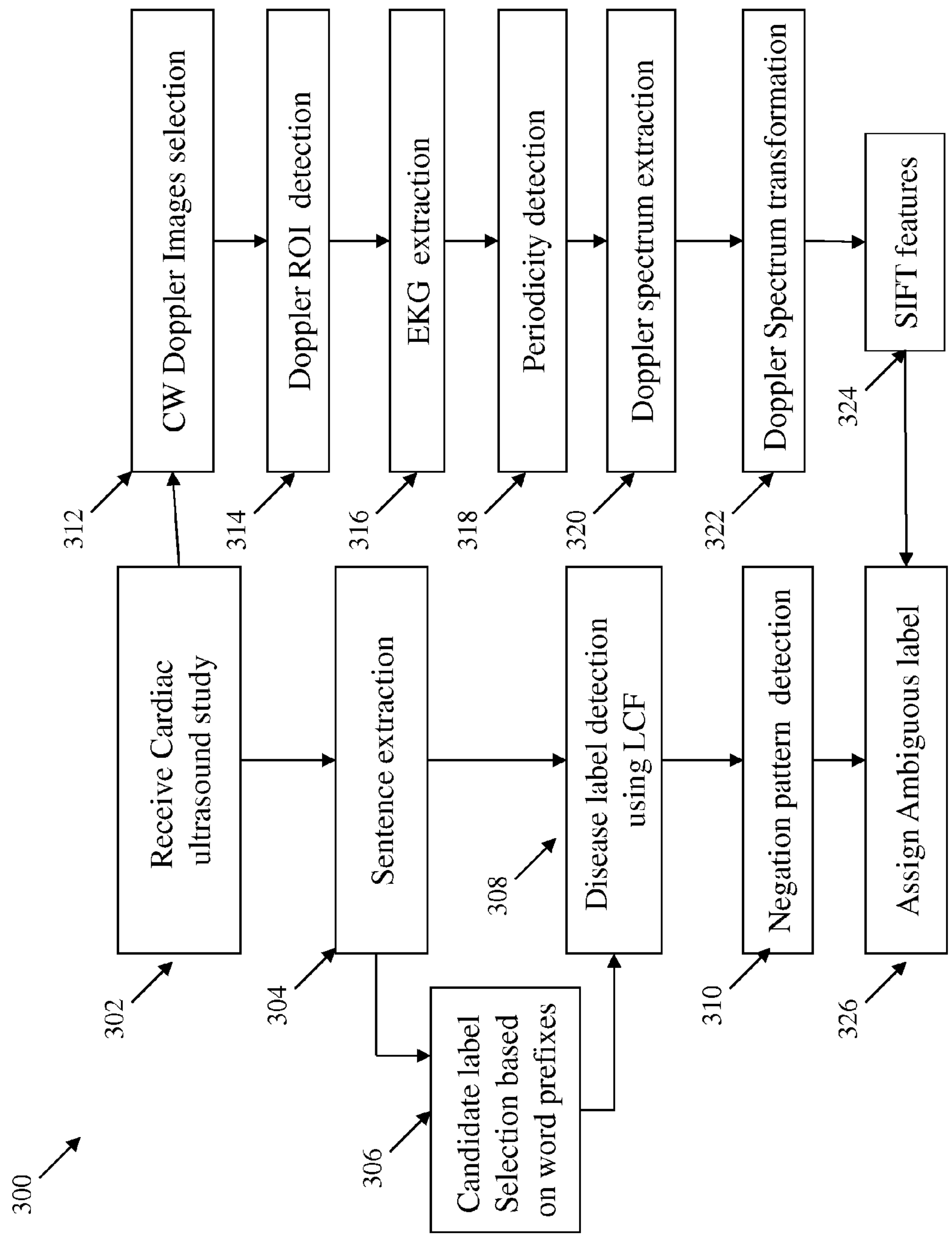
FIG. 3 depicts a flowchart diagram of a method for automatic ground truth generation of medical image collections in accordance with an exemplary embodiment.

Referring now to FIG. 3, a flowchart diagram of a method 300 for automatic ground truth generation of medical image collections in accordance with an exemplary embodiment is shown. As illustrated at block 302, the method 300 includes receiving a cardiac ultrasound study that includes a plurality of images and a textual report. As shown at block 304, the method 300 includes extracting sentences from the textual report. Next, as shown at block 306, the method 300 includes selecting candidate disease labels based word prefixes in the extracted sentences. The method 300 further includes detecting disease labels using a longest common subfix algorithm, as shown at block 308. Next, as shown at block 310, the method 300 includes using negation pattern detection to refine the detected disease labels. The method 300 further includes assigning an ambiguous label to an image from the cardiac ultrasound study based on the detected disease labels.

Continuing with reference to FIG. 3, the method 300 includes selecting a key image form the cardiac ultrasound study, as shown at block 312. Next, as shown at block 314, the method 300 includes detecting a region of interest (ROI) form the key image. Next, as shown at block 316, the method 300 includes extracting an electrocardiogram (EKG) from the ROI. The method 300 further includes detecting the periodicity of the EKG, as shown at block 318. Next, as shown at block 320, the method 300 includes extracting a Doppler spectrum from the ROI. The method 300 further includes performing a transformation on the extracted Doppler spectrum, as shown at block 322. Next, the method 300 includes and encoding the extract Doppler envelopes and their enclosing regions through Scale-Invariant Feature Transform (SIFT) code books.

Figure 6:
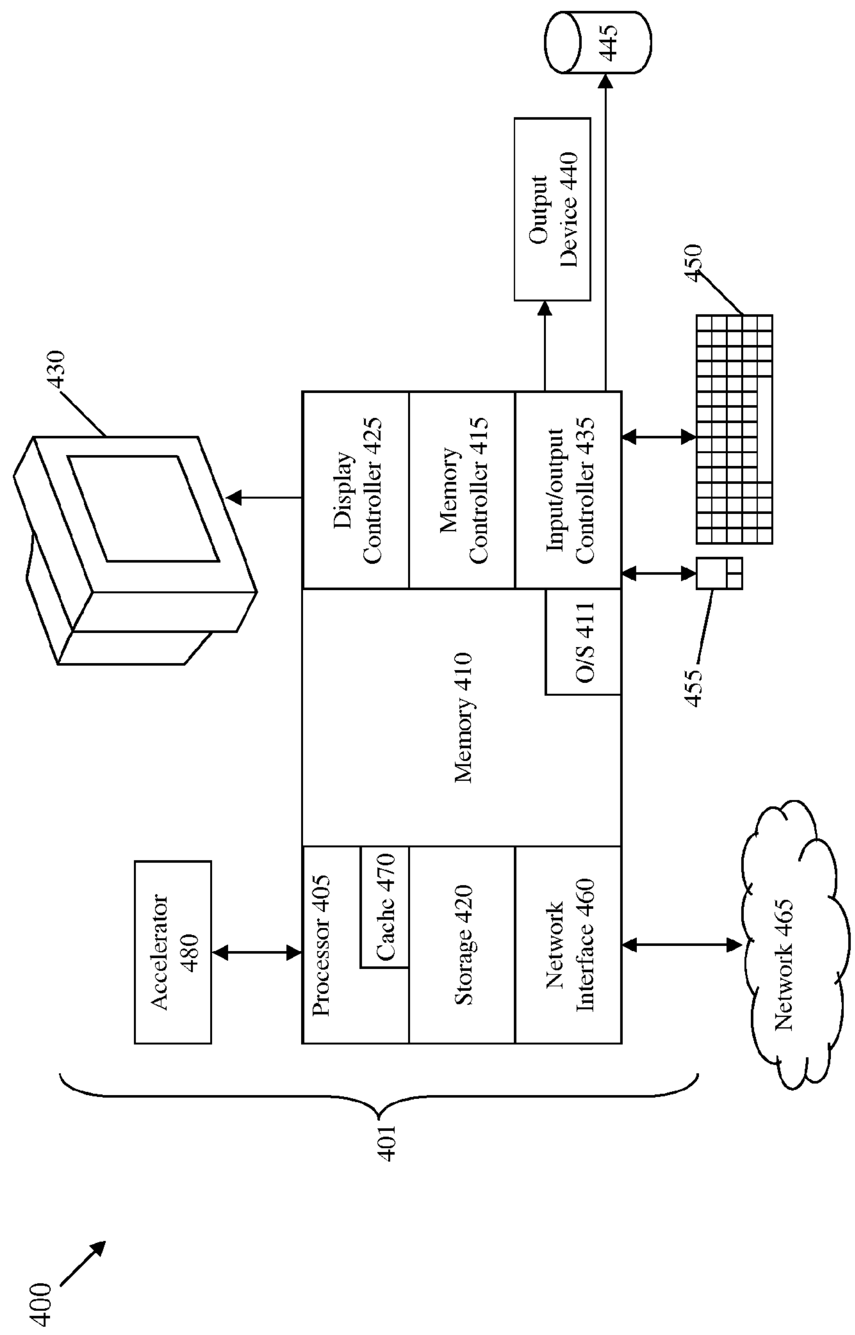
FIG. 6 depicts a block diagram of a computer system for practicing the teachings herein according to an embodiment.

Referring now to FIG. 6, a block diagram of an exemplary computer system 400 for use with the teachings herein is shown. The methods described herein can be implemented in hardware software (e.g., firmware), or a combination thereof. In an exemplary embodiment, the methods described herein are implemented in hardware, and is part of the microprocessor of a special or general-purpose digital computer, such as a personal computer, workstation, minicomputer, or mainframe computer. The system 400 therefore includes general-purpose computer 401.

In an exemplary embodiment, in terms of hardware architecture, as shown in FIG. 6, the computer 401 includes a processor 405, memory 440 coupled via a memory controller 445, a storage device 420, and one or more input and/or output (I/O) devices 440, 445 (or peripherals) that are communicatively coupled via a local input/output controller 435. The input/output controller 435 can be, for example, but not limited to, one or more buses or other wired or wireless connections, as is known in the art. The input/output controller 435 may have additional elements, which are omitted for simplicity, such as controllers, buffers (caches), drivers, repeaters, and receivers, to enable communications. Further, the local interface may include address, control, and/or data connections to enable appropriate communications among the aforementioned components. The storage device 420 may include one or more hard disk drives (HDDs), solid state drives (SSDs), or any other suitable form of storage.

The processor 405 is a computing device for executing hardware instructions or software, particularly that stored in memory 440. The processor 405 can be any custom made or commercially available processor, a central processing unit (CPU), an auxiliary processor among several processors associated with the computer 401, a semiconductor based microprocessor (in the form of a microchip or chip set), a macro-processor, or generally any device for executing instructions. The processor 405 may include a cache 470, which may be organized as a hierarchy of more cache levels (L1, L2, etc.).

The memory 440 can include any one or combination of volatile memory elements (e.g., random access memory (RAM, such as DRAM, SRAM, SDRAM, etc.)) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 440 may incorporate electronic, magnetic, optical, and/or other types of storage media. Note that the memory 440 can have a distributed architecture, where various components are situated remote from one another, but can be accessed by the processor 405.

The instructions in memory 440 may include one or more separate programs, each of which comprises an ordered listing of executable instructions for implementing logical functions. In the example of FIG. 6, the instructions in the memory 440 include a suitable operating system (OS) 411. The operating system 411 essentially controls the execution of other computer programs and provides scheduling, input-output control, file and data management, memory management, and communication control and related services.

In an exemplary embodiment, a conventional keyboard 450 and mouse 455 can be coupled to the input/output controller 435. Other output devices such as the I/O devices 440, 445 may include input devices, for example but not limited to a printer, a scanner, microphone, and the like. Finally, the I/O devices 440, 445 may further include devices that communicate both inputs and outputs, for instance but not limited to, a network interface card (NIC) or modulator/demodulator (for accessing other files, devices, systems, or a network), a radio frequency (RF) or other transceiver, a telephonic interface, a bridge, a router, and the like. The system 400 can further include a display controller 425 coupled to a display 430. In an exemplary embodiment, the system 400 can further include a network interface 460 for coupling to a network 465. The network 465 can be an IP-based network for communication between the computer 401 and any external server, client and the like via a broadband connection. The network 465 transmits and receives data between the computer 401 and external systems. In an exemplary embodiment, network 465 can be a managed IP network administered by a service provider. The network 465 may be implemented in a wireless fashion, e.g., using wireless protocols and technologies, such as Wi-Fi, WiMax, etc. The network 465 can also be a packet-switched network such as a local area network, wide area network, metropolitan area network, Internet network, or other similar type of network environment. The network 465 may be a fixed wireless network, a wireless local area network (LAN), a wireless wide area network (WAN) a personal area network (PAN), a virtual private network (VPN), intranet or other suitable network system and includes equipment for receiving and transmitting signals.

If the computer 401 is a PC, workstation, intelligent device or the like, the instructions in the memory 440 may further include a basic input output system (BIOS) (omitted for simplicity). The BIOS is a set of essential routines that initialize and test hardware at startup, start the OS 411, and support the transfer of data among the storage devices. The BIOS is stored in ROM so that the BIOS can be executed when the computer 401 is activated.

When the computer 401 is in operation, the processor 405 is configured to execute instructions stored within the memory 440, to communicate data to and from the memory 440, and to generally control operations of the computer 401 pursuant to the instructions. In exemplary embodiments, the computer system 400 includes one or more accelerators 480 that are configured to communicate with the processor 405. The accelerator 480 may be a field programmable gate array (FPGA) or other suitable device that is configured to perform specific processing tasks. In exemplary embodiments, the computer system 400 may be configured to offload certain processing tasks to an accelerator 480 because the accelerator 480 can perform the processing tasks more efficiently than the processor 405.

It should be noted that the flowchart and block diagrams in the figures illustrate the architecture, functionality, and operation of possible implementations of systems, apparatuses, methods and computer program products according to various embodiments of the invention. In this regard, each block in the flowchart or block diagrams may represent a module, segment, or portion of code, which comprises at least one executable instruction for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wirelesss transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure.

Although illustrative embodiments of the invention have been described herein with reference to the accompanying drawings, it is to be understood that the embodiments of the invention are not limited to those precise embodiments, and that various other changes and modifications may be affected therein by one skilled in the art without departing from the scope or spirit of the disclosure.

What is claimed is:

1. A method for automatic ground truth generation of medical image collections, the method comprising:

receiving a plurality of imaging studies, wherein each imaging study comprises one or more images and a textual report associated with the one or more images;

selecting a key image from each of the plurality of imaging studies;

extracting one or more discriminating image features from a region of interest within the key image;

processing the textual report associated with the one or more images to detect one or more concept labels;

assigning an initial label from the one or more concept labels to the one or more discriminating image features; and learning an association between each of the one or more discriminating image features and the one or more concept labels;

wherein learning the association between each of the one or more discriminating image features and the one or more concept labels comprises executing a convex optimization learning algorithm.

2. The method of claim 1 further comprising:

creating a set of frequently occurring concept labels based on the one or more concept labels detected in the textual reports.

3. The method of claim 2 wherein learning the association between each of the one or more discriminating image features and the one or more concept labels comprises determining if the initial label assigned to the one or more discriminating image features is within the set of frequently occurring concept labels.

4. The method of claim 1, wherein processing the textual report associated with the one or more images to detect the one or more concept labels comprises executing a longest common subfix algorithm on the textual report.

5. The method of claim 1, wherein the plurality of imaging studies are echocardiogram studies and the region of interest is a Doppler spectrum.

6. The method of claim 5, wherein extracting one or more discriminating image features includes densely sampling both an envelope and an interior of the Doppler spectrum using one or more scale-invariant feature transform features.

7. A computer program product for automatic ground truth generation of medical image collections, the computer program product comprising:

a computer readable storage medium having program code embodied therewith, the program code executable by a computer to:

receive a plurality of imaging studies, wherein each imaging study comprises one or more images and a textual report associated with the one or more images;

select a key image from each of the one or more images from each of the plurality of imaging studies;

extract one or more discriminating image features from a region of interest within the key image;

process the textual report associated with the one or more images to detect one or more concept labels;

assign an initial label from the one or more concept labels to the one or more discriminating image features; and learn an association between each of the one or more discriminating image features and the one or more concept labels;

wherein learning the association between each of the one or more discriminating image features and the one or more concept labels comprises executing a convex optimization learning algorithm.

8. The computer program product of claim 7, wherein the program code executable by the computer further creates a set of frequently occurring concept labels based on the one or more concept labels detected in the textual report.

9. The computer program product of claim 8, wherein learning the association between each of the one or more discriminating image features and the one or more concept labels comprises determining if the initial label assigned to the one or more discriminating image features is within the set of frequently occurring concept labels.

10. The computer program product of claim 7, wherein processing the textual report associated with the one or more images to detect the one or more concept labels comprises executing a longest common subfix algorithm on the textual report.

11. The computer program product of claim 7, wherein the plurality of imaging studies are echocardiogram studies and the region of interest is a Doppler spectrum.

12. The computer program product of claim 11 wherein extracting one or more discriminating image features includes densely sampling both an envelope and an interior of the Doppler spectrum using one or more scale-invariant feature transform features.

13. A computer system for automatic ground truth generation of medical image collections, the computer system comprising:

a processor configured to execute a program code causing the computer system to:

receive a plurality of imaging studies, wherein each imaging study comprises one or more images and a textual report associated with the one or more images;

select a key image from each of the plurality of imaging studies;

extract one or more discriminating image features from a region of interest within the key image;

process the textual report associated with the one or more images to detect one or more concept labels;

assign an initial label from the one or more concept labels to the one or more discriminating image features; and learn an association between each of the one or more discriminating image features and the one or more concept labels;

wherein learning the association between each of the one or more discriminating image features and the one or more concept labels comprises executing a convex optimization learning algorithm.

14. The computer system of claim 13, wherein the program code further causes the computer system to create a set of frequently occurring concept labels based on the one or more concept labels detected in the textual report.

15. The computer system of claim 14, wherein learning the association between each of the one or more discriminating image features and the one or more concept labels comprises determining if the initial label assigned to the one or more discriminating image features is within the set of frequently occurring concept labels.

16. The computer system of claim 13, wherein processing the textual report associated with the one or more images to detect the one or more concept labels comprises executing a longest common subfix algorithm on the textual report.

17. The computer system of claim 13, wherein the plurality of imaging studies are echocardiogram studies and the region of interest is a Doppler spectrum.

18. The computer system of claim 17 wherein extracting one or more discriminating image features includes densely sampling both an envelope and an interior of the Doppler spectrum using one or more scale-invariant feature transform features.

* * * * *